(12) United States Patent
Schapowalov et al.

(10) Patent No.: US 6,288,158 B1
(45) Date of Patent: Sep. 11, 2001

(54) MODIFIED SUPERABSORBENT POLYMER BASED ON POLYACRYLONITRILE EMULSIONS

(75) Inventors: Sergej Schapowalov, Mortsel (BE); Günter Sackmann; Rolf-Volker Meyer, both of Leverkusen (DE); Siegfried Korte, Odenthal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/247,748

(22) Filed: Feb. 9, 1999

(30) Foreign Application Priority Data

Feb. 11, 1998 (DE) .............................. 198 05 447

(51) Int. Cl.$^7$ ..................................... C08K 3/34
(52) U.S. Cl. .......................... 524/493; 524/379; 524/389; 524/492; 524/512; 524/565; 524/566; 525/328.7; 525/329.1; 525/342; 525/383; 523/204; 523/208; 523/209
(58) Field of Search ..................................... 524/493, 492, 524/566, 389, 379, 512, 565; 525/329.1, 328.7, 383, 342; 523/204, 208, 209

(56) References Cited

U.S. PATENT DOCUMENTS

| | | | |
|---|---|---|---|
| 3,981,100 | * 9/1976 | Weaver et al. | 47/58 |
| 4,228,056 | * 10/1980 | Stoy | 526/221 |
| 4,614,780 | * 9/1986 | Huhn et al. | 525/329.1 |
| 4,795,762 | 1/1989 | Diamantoglou et al. | 521/84.1 |
| 5,087,513 | * 2/1992 | Kim | 428/283 |
| 5,091,080 | * 2/1992 | Van Eikeren et al. | 210/188 |
| 5,302,314 | 4/1994 | Troglia et al. | 252/174.23 |
| 5,356,985 | 10/1994 | Sachmann et al. | 524/460 |
| 5,409,771 | 4/1995 | Dahmen et al. | 428/327 |
| 5,496,890 | 3/1996 | Sackmann et al. | 525/329.1 |
| 5,567,779 | 10/1996 | Sackmann et al. | 525/329.1 |
| 5,635,569 | 6/1997 | Sackmann et al. | 525/367 |
| 5,728,774 | 3/1998 | Sackmann et al. | 525/196 |
| 5,789,570 | 8/1998 | Buchholz et al. | 536/107 |

FOREIGN PATENT DOCUMENTS

| | | |
|---|---|---|
| 1090553 | 12/1980 | (CA) . |
| 716322 | 1/1942 | (DE) . |
| 4442605 | 6/1996 | (DE) . |
| 0 629 411 | 12/1994 | (EP) . |
| 2094809 | 9/1982 | (GB) . |

OTHER PUBLICATIONS

Database WPI, Sec. Ch, AN 96–493491, XP 002103734 & JP 08 253597 A (Nippon Synthetic Chem. Ind., Co.) Oct. 1, 1996.

Chemical Abstracts, vol. 110, No. 8, Feb. 20, 1989, Abstract No. 58375g XP000158099 & CN 86 104 111 A (China Petrochemical Corp.).

* cited by examiner

Primary Examiner—Judy M. Reddick
(74) Attorney, Agent, or Firm—Joseph C. Gil; Aron Preis

(57) ABSTRACT

A process for modifying superabsorbent polymers is disclosed. The surface of a polymer containing hydrolyzed polyacrylonitrile in the form of particulates, is modified by crosslinking in a water/alcohol reaction mixture and in the presence of silica. The resulting product features improved absorbency under load and lesser degree of gel blocking.

11 Claims, No Drawings

MODIFIED SUPERABSORBENT POLYMER BASED ON POLYACRYLONITRILE EMULSIONS

The present invention relates to superabsorbing polymers based on finely divided crosslinked or uncrosslinked polyacrylonitrile emulsions and to the improved applicational characteristics thereof.

Superabsorbing polymers are known and are primarily used in the production of diapers and incontinence articles, but are also used as water storage materials in agriculture and for sheathing electrical cables. Commercially available superabsorbing polymers are generally loosely crosslinked, water-insoluble polymers based on alkali metal salts of polyacrylic acid or on copolymers of acrylic acid and acrylamide, which are obtained by free-radically initiated copolymerization of acrylic acid and polyfunctional monomers, such as for example divinylbenzene, ethylene glycol dimethacrylate, ethylene glycol diallyl ether, butanediol acrylate, hexanediol methacrylate, polyglycol diacrylate, trimethylolpropane diacrylate, allyl acrylate, diallyl acrylamide, triallylamine, diallyl ether, methylenebisacrylamide and N-methylolacrylamide. By virtue of their molecular structure, such polymers are capable of absorbing large quantities of liquids by swelling and forming hydrogels and also of retaining these liquids under pressure.

European patent application EP-A 0,670,335 discloses that products having excellent superabsorbent properties may be produced by partial alkaline hydrolysis of finely divided aqueous emulsions of linear homo- and/or copolymers of acrylonitrile, in which products 30 to 60 mol. % of the nitrile groups have been converted into carboxylate groups, 20 to 60 mol. % of the nitrile groups have been converted into carbonamide groups and 10 to 20 mol. % of the nitrile groups remain unchanged. These uncrosslinked superabsorbing polymers exhibit an extraordinarily high swelling capacity of up to 1000 g/g in water and of up to 90 g/g in physiological sodium chloride solution. It is also known from EP-A 0,697,416 that superabsorbing polymers having excellent applicational characteristics may also be obtained by partial alkaline hydrolysis of finely divided aqueous emulsions of acrylonitrile homo- and/or copolymers weakly crosslinked by the incorporation of polyfunctional monomers. The superabsorbing polymers produced from crosslinked polyacrylonitrile emulsions, the nitrile groups of which have been converted to an extent of 30 to 80 mol. % into carboxylate groups, to an extent of 20 to 70 mol. % into carbonamide groups, and which polymers still contain between 0 and 20 mol. % of unchanged nitrile groups, are capable of absorbing up to 700 g/g of water and up to 60 g/g of physiological sodium chloride solution.

The finely divided, aqueous, uncrosslinked or crosslinked polyacrylonitrile emulsions required for the production of the superabsorbing polymers are obtained by homo- and/or copolymerizing acrylonitrile in the presence of special anionic polymeric emulsifiers (DE-OS 4,233, 026). The molecular weights of the uncrosslinked polyacrylonitrile emulsions produced using this process are within the range from $5 \times 10^5$ to $1 \times 10^7$ g/mol., preferably from $2 \times 10^6$ to $5 \times 10^6$ g/mol. The particle sizes of the uncrosslinked or crosslinked aqueous polyacrylonitrile emulsions are within the range between 100 and 300 nm, preferably between 100 and 200 nm (determined by laser correlation spectroscopy).

However, the superabsorbing polymers obtainable by partial alkaline hydrolysis of uncrosslinked or crosslinked aqueous polyacrylonitrile emulsions also exhibit some disadvantageous characteristics, among which a certain tendency towards "gel blocking" may in particular be mentioned. When these products are used in personal hygiene articles, such as for example diapers "gel blocking" results in a low initial transport rate of the liquid to be absorbed, which results in overall relatively poor liquid transport proper-ties and to low "absorbency under load", i.e. when exposed to elevated pressure of, for example, 0.7 psi, there is a perceptible decrease in the absorbency of the superabsorbent particles. Such a process ultimately also results in low "rewet" values of the nappies.

This "gel blocking" behavior is also known in superabsorbents based on polyacrylic acid. In order to avoid or overcome this characteristic, which has a negative impact on product performance, the superabsorbents may be treated, for example, with antiblocking agents, such as for example silica gel, cellulose fluff or other synthetic or natural hydrophilic fibers or also materials which have a greater surface area than the superabsorbents themselves (c.f. DE-OS 4,442, 606), Another method for avoiding the "gel blocking" behavior of superabsorbents is surface crosslinking of the superabsorbent particles with various crosslinking agents having at least two functional groups. DE-OS 4,020,780 accordingly mentions various alkylene carbonates, such as 1,3-dioxolan-2-one or 4-methyl-1,3-dioxolan-2-one as effective crosslinking agents, while DE-OS, 4,442,605 mentions aldehydes or also difunctional isocyanates. A feature common to all the methods listed therein is that, after surface crosslinking, the superabsorbents modified in this manner must be subjected to heat treatment at temperatures of between 150 and 300° C. in order to ensure that "gel blocking" is effectively prevented.

The object underlying the present invention was to avoid "gel blocking" and thus, to achieve an increase in the initial transport rate, an improvement in "absorbency under load" and the transport rate under load. This aim has been achieved according to the invention by performing surface crosslinking with difunctional compounds and simultaneously immobilizing silica in the surface structure of the superabsorbing polymers.

It has surprisingly been found that simultaneous crosslinking and immobilization of silica brings about a synergistic effect. This is manifested by a disappearance of "gel blocking" with a simultaneous increase in the initial transport rate and a distinct improvement in "absorbency under load" values at 0.3 and 0.7 psi.

Surface modification, which may also be described as immobilization, is performed on the already formed superabsorbent particles in a water/alcohol mixture with a water concentration of 2 to 15 wt. %, preferably of 6 to 12 wt. %, using formaldehyde or other aldehydes, for example glutaraldehyde, as crosslinking agents in the presence of silica. The already formed superabsorbent particles, used as starting materials are prepared by polymerizing a latex emulsion (in water), precipitating the polymer particles, drying them, grinding and sieving the product obtained as described in U.S. Pat. Nos. 5,496,890 and 5,635,569 incorporated herein by reference. Such particles, while superabsorbent, still show gel-blocking. In the inventive process, the surface of these particles is modified in an aqueous alcoholic medium by reaction with silica and an aldehyde (which acts as a crosslinking agent). The resulting modified particles show improved "absorbency under load" and a lesser degree of gel blocking. The silica suitable in the inventive process may be in solid or liquid form, preferably as colloidal silica in solution. Most preferably the silica is in the form of colloidal solution having a concentration of 15 to 30 wt. %, particle diameter of 5 to 50 nm, preferably 5 to 30 nm, specific surface of 1 00 to 450 m$^2$/g and pH value of 4 to 6. The concentration of formaldehyde in the reaction mixture used to modify the superabsorbent is here 0.1 to 2.0 wt. %, preferably 0.3 to 1.0 wt. %, and the concentration of silica is between 0.3 and 2.0 wt. %, preferably 0.5 to 1.5 wt. % the percents being relative to the weight of the reaction mixture. Alcohols which may be used are methanol, ethanol, n-propanol, i-propanol or also mixtures of the stated alcohols, but preferably methanol or ethanol, at a liquid/solid ratio of 0.1 to 10, preferably of 0.2 to 1, and a solids content after filtration before drying of 50 to 90 wt. %, preferably of 70 to 85 wt. %. The drying temperature of the superabsorbing polymers treated with the above-stated reaction mixture is 60 to 120° C., preferably 80 to 100° C. The concentration of the water in the reaction mixture is dependent upon the liquid/solid ratio. If water contents are above 15%, agglomeration of secondary particles occurs on drying. The superabsorbing polymers according to the invention are preferably characterized in that they contain, as a result of the invention process, 0.03 to 0.6 wt. % aldehycle, 0.05 to 0.8 wt. % silica, and 0.5 to 8.0 wt. % water, the percents being relative to the weight of the superabsorbing polymer, used, for example, in personal hygiene products, such as for example, diapers and incontinence articles, as water storage materials in agriculture and for sheathing electrical cables.

The invention is further illustrated but is not intended to be limited by the following examples in which all parts and percentages are by weight unless otherwise specified.

EXAMPLES

Production of the Hydrolysis Products

The following products A to E described below were used as the starting materials on which the modifications were performed. They were produced by alkaline hydrolysis with an aqueous NaOH solution. The silica used in the examples was a colloidal solution having a solid content of 15%, particle size of about 30 nm and pH of 5.0. The amounts of silica and formaldehyde noted in the examples refer to the pure substances.

Product A:

963.6 g of a polyacrylonitrile emulsion, 0.75 wt. % crosslinked relative to the acrylonitrile, having an average particle size of 93 nm and a solids content of 21.7 wt. %, were initially introduced together with 529.6 g of ethanol into a 2 liter stirred vessel with a reflux condenser, dropping funnel, thermometer and nitrogen inlet. 177.7 g of a 45 wt. % aqueous NaOH solution are then added dropwise with stirring at a rotational speed of 250 rpm. On heating to 76 to 78° C., the reaction mixture began to change color to dark red with elimination of NH$_3$. The eliminated ammonia was removed from the reaction flask and passed into an absorption flask filled with water. The course of the reaction may be monitored quantitatively by titrating the absorbed NH$_3$ with 1 N HCl. At a degree of hydrolysis of 59.5 mol. %, which was reached after approx. 3 hours, the light yellow to white reaction mixture was cooled to room temperature and the excess NaOH neutralized with aqueous formic acid. The reaction product was precipitated by adding 500 g of ethanol and the resultant suspension filtered out and washed with a water/ethanol mixture on the vacuum filter. After drying in a drying cabinet at 65° C., the product was ground and classified by screening. The diameters of the particles were between 100 and 800 μm.

Product B:

In this case, an uncrosslinked polyacrylonitrile emulsion having an [η] value of 9.02 (dl/g) (measured in DMF with addition of electrolyte), an average particle size of 82 nm and a solids content of 20.0 wt. % was used for the hydrolysis. The reaction was performed under the following conditions: PAN concentration in the reaction mixture: 11.0 wt. %, NaOH concentration in the reaction mixture: 5.81 wt. %, i.e., a molar ratio of PAN:NaOH of 1:0.7. The reaction proceeded in water without addition of ethanol at 95° C. After a residence time of 1.5 hours, the degree of hydrolysis was 57.7 mol. %.

Product C:

Product C was obtained from product B once B had been heat treated at 180° C. for 15 minutes.

Product D:

Product D was produced using the same process as for product A. The uncrosslinked polyacrylonitrile emulsion used in this case for hydrolysis had a solids content of 31.5 wt. %, an average particle size of 115 nm and an [η] value of 932 dl/g). After a residence time of 2.25 hours, the degree of hydrolysis was 54.0 mol. %.

Product E:

Product E was produced using the same process as for products A and D, likewise in a water/ethanol mixture. The uncrosslinked polyacrylonitrile emulsion used had a solids content of 30.0 wt. %, an [η] value of 9.2 (dl/g) and an average particle size of 120 nm. After a residence time of 3 hours, the degree of hydrolysis was approx. 63 mol. %.

Modification of the Hydrolysis Products

Hydrolysis products A to E, which had particle diameters in the range from 100 to 800 μm, were modified using the following general method:

Example 1

35 g of product A were stirred for 20 minutes at room temperature with 200 g of a reaction mixture of the following composition:

178.0 g of methanol 18.0 g of deionized water 3.0 g of silica 1.0 g of formaldehyde.

After filtration through a vacuum filter, the crude product having a solids content of 70.1 wt. % was dried for 30 minutes at 98° C. in a circulating air cabinet.

Comparative Examples I–IV

Comparative Examples I–IV are intended to demonstrate the synergistic effect brought about by the simultaneous crosslinking and immobilization of silica.

Comparative Example 1

35 g of product A, which had a defined particle size distribution, were stirred for 20 minutes at room temperature with 200 g of a reaction mixture of the following composition:

182.0 g of methanol 18.0 g of deionized water.

After filtration through a vacuum filter, the crude product having a solids content of 70.1 wt. % was dried for 45 minutes at 98° C.

Comparative Example II

Treatment (20 minutes at room temperature) of 35 g of product A with 200 g of a reaction mixture of the following composition:

179.0 g of methanol 18.0 g of deionized water 3.0 g of silica. solids content after filtration: 70.1 wt. %; drying at 98° C. (45 minutes).

Comparative Example III 35 g of product A were treated for 20 minutes with the following reaction mixture:

181.0 g of methanol
18.0 g of deionized water
1.0 g of formaldehyde.

Solids content after filtration: 70.2 wt. % drying at 98° C. (45 minutes).

Comparative Example IV 20 g of the product from Comparative Example III were stirred for 20 minutes at room temperature with 114.8 g of a reaction mixture of the following composition:

182.8 g of methanol
10.4 g of deionized water
1.8 g of silica

After filtration, the solids content was 70.3 wt. %; drying was performed at 98° C. for 45 minutes.

Example 2

100 g of product B were stirred for 20 minutes at room temperature with 570 g of a reaction mixture of the following composition:

507.3 g of methanol
51.3 g of deionized water
8.0 g of silica
3.4 g of formaldehyde.

After filtration, the modified hydrolyzate having a solids content of 70.3 wt. % was dried for 45 minutes at 98° C.

Example 3

Example 3 was performed using the same method as Example 2, but with the difference that product C was used instead of product B for the modification.

Example 4

100 g of product D are reacted for 5 minutes at room temperature with 570 g of a reaction mixture of the following composition:

507.3 g of methanol
51.3 g of deionized water
8.6 g of silica
2.8 g of formaldehyde.

After filtration, the crude product having a solids content of 70.3 wt. % was dried for 45 minutes at 98° C.

Example 5

1025 g of product E were stirred for 10 minutes at room temperature with a reaction mixture of the following composition:

1368.8 g of ethanol
138.4 g of deionized water
15.4 g of silica
15.4 g of formaldehyde.

After filtration, the modified product having a solids content of 75.9 wt. % was dried for 2 hours at 90° C.

Table 1 below summarizes the applicational characteristics of the modified superabsorbents obtained according to Examples 1 to 5. The following characteristics were assessed:

Absorption in accordance with the cylinder method as described in DE-OS 4,015,085; on-line measurements were taken every 2 seconds. Table 1, however, only shows the values after 15 seconds, 3 minutes, 10 minutes and 30 minutes.

Absorption in accordance with the tea bag method (according to "edana" 440.0-96).

Retention (C. C.); (according to "edana" 441.0-96).

AUL (absorbency under load) at 0.3 psi and 0.7 psi (according to "edana" 442.0-96).

Initial absorption rate, calculated from the linear section of the absorption curves.

The Table also states the water-soluble fractions (WSF), which were determined by extraction and gravimetric determination of the evaporation residues, and the pH value. All testing was performed using 0.95 NaCl solution.

By way of comparison, the Table also shows examples 1A to 5E, these respectively being the unmodified products A to E, from which Examples 1 to 5 were produced.

The last four lines of Table 1 additionally show the results obtained with Comparative Examples I to IV.

TABLE 1

| | Initial absorption rate | Absorption (cylinder) [g/g] | | | | Absorption (tea bag) [g/g] | | | Retention | AUL [g/g] | | | | WSF | pH |
| | | | | | | | | | | 0.3 psi | | 0.7 psi | | | |
| Example | [g/g/sec] | 15 sec | 3 min | 10 min | 30 min | 15 sec | 3 min | 10 min | [g/g] | 3 min | 30 min | 3 min | 30 min | [wt. %] | value |
| --- | --- | --- | --- | --- | --- | --- | --- | --- | --- | --- | --- | --- | --- | --- | --- |
| 1 | 0.66 | 9.9 | 30.0 | 42.0 | 47.0 | 9.8 | 36.5 | 47.6 | 34.2 | 15.0 | 29.9 | 10.5 | 23.0 | 4.5 | 6.08 |
| 1A | 0.18 | 2.7 | 24.0 | 36.9 | 43.3 | 2.4 | 30.5 | 49.0 | 42.0 | 2.0 | 6.0 | 1.7 | 4.5 | 7.0 | 6.12 |
| 2 | 0.70 | 10.5 | 32.0 | 40.0 | 50.4 | 11.0 | 39.7 | 53.7 | 38.0 | 15.0 | 29.3 | 10.3 | 18.0 | 8.9 | 6.24 |
| 2B | 0.12 | 1.7 | 17.3 | 28.0 | 35.6 | 2.0 | 30.5 | 50.0 | 49.5 | 1.5 | 4.3 | 1.5 | 3.8 | 12.0 | 6.30 |
| 3 | 0.73 | 11.2 | 34.0 | 45.0 | 50.1 | 11.0 | 42.1 | 49.5 | 32.0 | 16.0 | 30.7 | 11.0 | 22.4 | 7.8 | 6.4 |
| 3C | 0.20 | 3.1 | 22.5 | 32.5 | 43.6 | 2.1 | 34.5 | 51.4 | 39.0 | 2.5 | 7.9 | 2.0 | 6.5 | 10.1 | 6.45 |
| 4 | 0.72 | 10.5 | 33.5 | 42.0 | 45.5 | 10.9 | 39.0 | 47.6 | 32.0 | 21.0 | 30.9 | 14.0 | 23.8 | 2.9 | 6.21 |
| 4D | 0.30 | 4.5 | 29.0 | 40.1 | 45.5 | 4.9 | 32.0 | 47.5 | 37.1 | 2.0 | 6.0 | 1.8 | 5.0 | 3.5 | 6.25 |
| 5 | 0.74 | 11.0 | 38.0 | 42.0 | 47.3 | 11.7 | 39.2 | 47.7 | 32.0 | 19.0 | 29.8 | 13.8 | 24.9 | 5.0 | 6.13 |
| 5E | 0.31 | 4.5 | 29.1 | 40.3 | 45.5 | 4.7 | 32.0 | 47.5 | 36.9 | 2.1 | 5.9 | 2.0 | 5.0 | 6.5 | 6.15 |

TABLE 1-continued

| | Absorption (cylinder) [g/g] | | | | | Absorption (tea bag) [g/g] | | | Retention | AUL [g/g] | | | | | |
|---|---|---|---|---|---|---|---|---|---|---|---|---|---|---|---|
| | Initial absorption rate | | | | | | | | | 0.3 psi | | 0.7 psi | | WLF | pH |
| Example | [g/g/sec] | 15 sec | 3 min | 10 min | 30 min | 15 sec | 3 min | 10 min | [g/g] | 3 min | 30 min | 3 min | 30 min | [wt. %] | value |
| I | 0.18 | 2.7 | 24.6 | 34.5 | 40.5 | 2.5 | 29.9 | 49.8 | 40.3 | 2.2 | 6.2 | 1.7 | 4.3 | 6.8 | 6.12 |
| II | 0.27 | 4.1 | 30.0 | 41.0 | 48.2 | 3.8 | 31.2 | 50.9 | 41.0 | 4.0 | 6.5 | 2.2 | 4.3 | 7.3 | 6.12 |
| III | 0.36 | 5.4 | 27.0 | 35.0 | 40.6 | 5.9 | 30.6 | 50.0 | 34.0 | 12.5 | 28.0 | 9.0 | 21.0 | 44 | 6.10 |
| IV | 0.44 | 6.6 | 27.0 | 36.0 | 43.8 | 6.7 | 31.5 | 49.0 | 34.2 | 12.9 | 28.3 | 9.2 | 21.0 | 4.6 | 6.10 |

It is very clearly evident from the result summarized in Table 1 that, in comparison with the unmodified superabsorbents, the modification according to the invention brings about a significant increase both in the initial absorption rates (c.f. column 2 of the Table), when measured both using the cylinder method and the tea bag method, and in the AUL values. The water soluble fraction values in the modified products are moreover substantially lower than in the unmodified products.

It is very obvious from the results of the products obtained according to Comparative Examples I to IV that the simultaneous modification with silica and formaldehyde results in a simultaneous increase in the initial transport rate under pressure and the AUL values (comparison between I-IV and Example 1). As a comparison of III and IV with Example 1 furthermore shows. simultaneous crosslinking and immobilization of silica not only increase the AUL values, but also bring about an increase in the initial transport rate with and without pressure and a reduction of the gel blocking effect.

Results of Rewet Measurements

Rewet measurements were performed on the superabsorbing polymers produced according to Examples 2, 3 and 5 in comparison with the unmodified Examples 2B, 3C and 5E.

The purpose of rewet measurements is to prove that, under practical conditions, for example for use in diapers, the superabsorbing polymers are capable of retaining body fluids even under pressure. In these measurements, 5 g of superabsorbent are uniformly distributed in cellulose fluff of an area of 13'21 cm and 70 ml of a 0.9% NaCl solution are then poured on. The surface is then covered with a stack of filter paper and a weight of 4 kg is placed thereon for 15 seconds. Once the increase in weight of the filter paper has been measured, the procedure (addition of 70 ml of liquid and repeated application of 4 kg) is repeated twice more. The increase in weight of the filter papers measured after each test is a measure of the capability of the superabsorbents to retain liquid even under elevated loads.

Table 2 below summarizes the measurements obtained.

TABLE 2

| | Rewet [g] | | |
|---|---|---|---|
| Example | 1st measurement | 2nd measurement | 3rd measurement |
| 2B | 0.05 | 2.04 | 4.19 |
| 2 | 0.04 | 0.38 | 1.21 |
| 3C | 0.05 | 1.94 | 3.67 |
| 3 | 0.04 | 0.18 | 0.75 |

TABLE 2-continued

| | Rewet [g] | | |
|---|---|---|---|
| Example | 1st measurement | 2nd measurement | 3rd measurement |
| 5E | 0.04 | 1.50 | 3.40 |
| 5 | 0.02 | 0.09 | 0.39 |

It is clearly evident that the modification brings about significantly reduced values for liquid release under pressure, especially after the $2^{nd}$ and $3^{rd}$ measurement. This indicates that "gel blocking" is greatly reduced or absent in the modified superabsorbing polymers.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for modifying a superabsorbent polymer containing hydrolyzed polyacrylonitrile in the form of particulates comprising crosslinking of the surface of said superabsorbent polymer in a water/alcohol reaction mixture and in the presence of silica.

2. The process of claim 1 wherein said crosslinking is effected with at least one difunctional compound.

3. The process of claim 1 wherein crosslinking is effected by an aldehyde.

4. The process of claim 3 wherein said aldehyde is formaldehyde.

5. The process of claim 2 wherein said compound is glutaraldehyde.

6. The process of claim 1 wherein said particulates have a diameter of about 100 to 800 microns.

7. The process of claim 1 wherein said crosslinking is effected with 0.1 to 2.0 percent of aldehyde, and said silica is present in an amount of 0.3 to 2.0 percent the percent, both occurrences being relative to the weight of said reaction mixture.

8. The process of claim 7 wherein said aldehyde is formaldehyde.

9. The process of claim 1 wherein said silica has a particle size of 10 to 50 nm.

10. The product prepared by the process of claim 1.

11. A method of using the product of claim 10 as an absorber in an application selected from the group consisting of personal hygiene, water storage and sheathing of an electrical cable.

* * * * *